United States Patent
Slivka et al.

(10) Patent No.: US 10,004,610 B2
(45) Date of Patent: Jun. 26, 2018

(54) NON-INVASIVE METHODS FOR MODIFYING TISSUE TO FACILITATE TREATMENT

(71) Applicant: DePuy Synthes Products, Inc., Raynham, MA (US)

(72) Inventors: Michael Slivka, Berkley, MA (US); Kevin Lee, Canton, MA (US); Roman Lomeli, Plymouth, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 669 days.

(21) Appl. No.: 14/613,502

(22) Filed: Feb. 4, 2015

(65) Prior Publication Data
US 2016/0220393 A1    Aug. 4, 2016

(51) Int. Cl.
*A61B 18/00* (2006.01)
*A61F 2/46* (2006.01)
(Continued)

(52) U.S. Cl.
CPC ............ *A61F 2/4675* (2013.01); *A61B 17/70* (2013.01); *A61B 18/12* (2013.01); *A61F 2/44* (2013.01);
(Continued)

(58) Field of Classification Search
CPC A61B 2018/00339; A61B 2018/00565; A61B 2018/00577; A61F 2017/0025–2017/0027
See application file for complete search history.

(56) References Cited

U.S. PATENT DOCUMENTS 6,264,651 B1 * 7/2001 Underwood ........... A61B 18/12
    604/114
6,607,498 B2    8/2003 Eshel et al.
(Continued)

FOREIGN PATENT DOCUMENTS

WO    2008/144274 A2    11/2008

OTHER PUBLICATIONS

[No Author Listed] Cleveland Clinic Ultrasound Lab. Retrieved from <http://focused-ultrasound.org/> on Feb. 29, 2016, 3 pages.
(Continued)

*Primary Examiner* — Nicholas Woodall
(74) *Attorney, Agent, or Firm* — Nutter McClennen & Fish LLP

(57) ABSTRACT

Systems and methods for facilitating treatment are disclosed that can include the use of imaging techniques in conjunction with one or more non-invasive techniques for modifying tissue, e.g., tissue in or around the spine. Depending on the type of treatment to be performed, various imaging modalities may be suitable for visualizing the tissue. Energy can be applied to tissue from outside of the body such that the tissue is modified in a non-invasive manner. For example, focused ultrasound can be used to dissect body tissues or can be applied to specific regions of tissue to change a characteristic of the tissue, e.g., increase its elasticity. The methods disclosed herein can be stand-alone treatments or can be performed prior to one or more surgical procedures. For example, non-invasive imaging and modification of body tissues can facilitate accessing the spine, preparing an interbody space, and/or surgically correcting the spine.

31 Claims, 8 Drawing Sheets

(51) Int. Cl.
*A61B 18/12* (2006.01)
*A61F 2/44* (2006.01)
*A61B 17/70* (2006.01)
*A61F 5/02* (2006.01)
*A61N 7/02* (2006.01)
*A61B 17/56* (2006.01)
*A61B 90/00* (2016.01)

(52) U.S. Cl.
CPC ............ *A61F 5/02* (2013.01); *A61N 7/02* (2013.01); *A61B 2017/564* (2013.01); *A61B 2018/0044* (2013.01); *A61B 2018/00339* (2013.01); *A61B 2018/00404* (2013.01); *A61B 2018/00434* (2013.01); *A61B 2018/00565* (2013.01); *A61B 2018/00577* (2013.01); *A61B 2090/374* (2016.02); *A61B 2090/376* (2016.02); *A61B 2090/378* (2016.02); *A61B 2090/3762* (2016.02)

(56) References Cited

U.S. PATENT DOCUMENTS

| | | | |
|---|---|---|---|
| 7,104,986 B2 * | 9/2006 | Hovda | A61B 18/12 128/898 |
| 7,510,536 B2 * | 3/2009 | Foley | A61B 8/06 600/439 |
| 8,057,408 B2 | 11/2011 | Cain et al. | |
| 8,333,700 B1 | 12/2012 | Barthe et al. | |
| 8,343,050 B2 * | 1/2013 | Fan | A61B 8/0833 600/437 |
| 8,357,095 B2 | 1/2013 | Anderson et al. | |
| 8,715,209 B2 * | 5/2014 | Gertner | A61B 8/06 600/407 |
| 9,149,658 B2 * | 10/2015 | Barthe | A61N 7/02 |
| 2014/0100459 A1 * | 4/2014 | Xu | A61B 17/2258 600/439 |

OTHER PUBLICATIONS

[No Author Listed] Focused Ultrasound Foundation. Retrieved from <http://www.fusfoundation.org/> on Feb. 29, 2016, 2 pages.

[No Author Listed] International Society for Therapeutic Ultrasound. Retrieved from <http://www.istu.org/> on Feb. 29, 2016, 2 pages.

[No Author Listed] medicalphysicsweb. IOP Publishing. Retrieved from <http://medicalphysicsweb.org/> on Feb. 29, 2016, 3 pages.

Abdullah, B.J., et al., Robot-assisted radiofrequency ablation of primary and secondary liver tumours: early experience. Eur Radiol. Jan. 2014;24(1):79-85. doi: 10.1007/s00330-013-2979-7. Epub Aug. 9, 2013.

Baac, H.W., et al., Carbon-nanotube optoacoustic lens for focused ultrasound generation and high-precision targeted therapy. Sci Rep. 2012;2:989. doi: 10.1038/srep00989. Epub Dec. 18, 2012.

Beasley, R., Medical robots: Current systems and research directions. Journal of Robotics, 2012, vol. 12, 14 pages.

Cleary, K., et al., Interventional robotic systems: Applications and technology state-of-the-art. Minimally Invasive Therapy and Allied Technologies, 2006, vol. 15, issue 2, pp. 101-113.

Dewall, R., et al., Visualizing tendon elasticity in an ex vivo partial tear model. Ultrasound Med Biol. Jan. 2014;40(1):158-67. doi: 10.1016/j.ultrasmedbio.2013.08.022. Epub Nov. 7, 2013.

Duggan-Jahns, T., Practical considerations in magnetic resonance imaging contrast studies. eRadimaging, 2009, 15 pages. Retrieved from <https://www.eradimaging.com/site/article.cfm?ID=736#.VumLEGf2Y-e>.

Karlo, C.A., et al., MR/CT image fusion of the spine after spondylodesis: a feasibility study. Eur Spine J. Oct. 2010;19(10):1771-5. doi: 10.1007/s00586-010-1430-x. Epub May 15, 2010.

Kim, Y.S., et al., High-intensity focused ultrasound therapy: an overview for radiologists. Korean J Radiol. Jul.-Aug. 2008;9(4):291-302. doi: 10.3348/kjr.2008.9.4.291.

Krafft, A.J., et al., A long arm for ultrasound: a combined robotic focused ultrasound setup for magnetic resonance-guided focused ultrasound surgery. Med Phys. May 2010;37(5):2380-93.

Lovric, V., et al., The effects of low-intensity pulsed ultrasound on tendon-bone healing in a transosseous-equivalent sheep rotator cuff model. Knee Surg Sports Traumatol Arthrosc. Feb. 2013;21(2):466-75. doi: 10.1007/s00167-012-1972-z. Epub Mar. 31, 2012.

Rieke, V., et al., MR thermometry. J Magn Reson Imaging. Feb. 2008;27(2):376-90. doi: 10.1002/jmri.21265.

Su, H., et al., High-field MRI-compatible needle placement robots for prostate interventions: Pneumatic and piezoelectric approaches. Gulrez, T., et al., eds., Advances in Robotics and Virtual Reality, Springer Verlag, 2011, Chapter 1, 30 pages.

Tempany, C., Focused ultrasound surgery in oncology: overview and principles. Radiology. Apr. 2011;259(1):39-56. doi: 10.1148/radiol.11100155.

Vlaisavljevich, E., et al., The effect of histotripsy on tissues with different mechanical properties. Ultrasonics Symposium (IUS), 2011 IEEE International, Oct. 18-21, 2011, Orlando, Florida, pp. 1490-1493.

Wells, P.N., et al., Medical ultrasound: imaging of soft tissue strain and elasticity. J R Soc Interface. Nov. 7, 2011;8(64):1521-49. doi: 10.1098/rsif.2011.0054. Epub Jun. 16, 2011.

Yeh, C.L., et al., Imaging monitored loosening of dense fibrous tissues using high-intensity pulsed ultrasound. Phys Med Biol. Oct. 7, 2013;58(19):6779-96. doi: 10.1088/0031-9155/58/19/6779. Epub Sep. 10, 2013.

* cited by examiner

NON-INVASIVE METHODS FOR MODIFYING TISSUE TO FACILITATE TREATMENT

FIELD

Methods for modifying tissue are disclosed herein, for example, methods for modifying tissue in and/or surrounding the spine to facilitate subsequent treatment.

BACKGROUND

Surgery can be the best option for treating various diseases and/or for treating traumatic injuries to a patient, yet even minimally-invasive surgical procedures can result in trauma to various anatomical structures and other risks. Iatrogenic injury can occur such as excessive bleeding, ischemia, infection, and nerve injury. As nerves are being separated from scar tissue or adjacent tissue, surrounding blood vessels and/or nerves can be unintentionally injured. Ischemia and/or nerve injury can also result from prolonged tissue retraction, which can be necessary when a surgeon is separating tissues to access a surgical site. As the duration of surgery increases, the risk of excessive blood loss and infection can also increase.

Surgical procedures involving the spine typically require that a surgeon identify and manipulate various regions and types of tissue. For example, a surgeon can separate or dissect tissue to create a pathway to a surgical site and/or to create space for insertion of an implant. Creating a desired pathway can be cumbersome, time-consuming and require extensive surgical exploration. This process can also cause unintended damage to tissue surrounding the pathway. Once the surgeon has access to the spine, tissue in or around the spine can be manipulated in various ways. For example, spinal fusion is a common method of treating patients with severe back pain. Exemplary fusion procedures can include removing the disc material prior to inserting a fusion cage and adding bone growth material into the disc space, which can then grow into a solid and stable construct. However, removal of the disc can be a difficult and time consuming process and can cause iatrogenic injury to the surrounding tissue. Other exemplary procedures that require dissection and/or separation of tissue include laminectomies and spinal disc replacements.

It is often necessary or desirable to perform revision surgery in which a treatment performed in a prior surgery is corrected in some way (e.g., adding additional implant hardware to a previously-implanted construct, removing previously-implanted implants, adjusting a previously-implanted construct, etc.). Revision surgeries can be associated with additional risks. For example, scar tissue and adhesions may form on vital structures such as blood vessels and nerves after the original surgery. This can make creating surgical access to the target site very difficult and dangerous since it is difficult to differentiate the scar tissue from the vital structures and often the scar tissue needs to be tediously dissected away, potentially causing prolonged surgery time.

Tissue in or surrounding the spine can cause the spine to resist surgical correction. While screws, rods, and other stabilization components can help correct the deformity, untreated surrounding tissue can restrict the ability of these implants to correct the spine and can thus interfere with the desired surgical outcome.

Accordingly, there is a continual need for systems and methods that are less invasive to a patient and that can reduce the risks and challenges of correcting pathologies via a surgical procedure.

SUMMARY

Systems and methods for correcting a pathology are disclosed herein. Such systems and methods can include non-invasively applying focused energy to target tissue to facilitate subsequent treatment on the patient to correct the pathology. The systems and methods can generally include imaging at least one region of a patient's body that includes tissue to be modified to identify a target tissue, non-invasively applying energy to the target tissue from a location outside of the patient's body to modify the target tissue, and after the target tissue has been modified, performing a treatment on the patient. Modifying the target tissue can facilitate performing the treatment.

The energy can be applied using various techniques, such as focused energy ablation, focused ultrasound, focused radiation, and RF electromagnetic energy delivery. The non-invasive energy application can facilitate the subsequent invasive or non-invasive treatment. The methods disclosed herein can be used to define a surgical access path, dissect scar tissue in advance of a revision surgery, strip soft tissue from bone, segment a spinal disc or other anatomical structure to facilitate removal, perform soft tissue release in connection with deformity correction procedures, separate implants from body tissues prior to revision surgery, or to perform any of a variety of other tasks that facilitate the treatment and the correction of a pathology.

The applied focused energy can create various changes in the tissue. For example, application of the focused energy can alter the elasticity of the tissue. Application of the focused energy can increase the elasticity of tissue. Application of the focused energy can ablate the tissue. Various imaging techniques can be used to image a region of the patient's body, e.g., the spine. For example, imaging the at least one region of the patient's spine can be performed using at least one of MRI, CT, fluoroscopy, and ultrasound. The focused energy can be applied using at least one of focused energy ablation, focused ultrasound, focused radiation, and RF electromagnetic energy delivery The application of the energy can define an access path. The application of the energy can cause the tissue along the access path to be visually distinguishable from surrounding tissue that has not been treated with focused energy. Modifying the tissue can include creating a plurality of landmarks to define the access path. The treatment can include surgically dissecting the tissue along the path defined by the plurality of landmarks.

Applying the focused energy can be effective to strip soft tissue off of a bone structure of the patient and/or to separate the target tissue from an implant. For example, the bone structure can be a lamina of a patient and the treatment can include performing a laminectomy on the patient after the soft tissue is stripped from the lamina. For another example, the target tissue can include tissue adjacent to a device implanted in the patient and application of the focused energy can separate the target tissue from the device. For yet another example, target tissue can include scar tissue and/or an adhesion and application of the focused energy separates the scar tissue and/or adhesion from at least one of a vessel, a nerve, and a dura of a patient.

In some embodiments, a method for treating a patient's spine includes imaging at least a portion of a patient's spine to identify tissue to be treated, non-invasively applying energy to the identified tissue from a location outside of the patient's body to modify the tissue, and performing a treatment on the modified tissue after the energy has been non-invasively applied. The non-invasive application of energy can facilitate the treatment.

Modifying the tissue can include at least one of altering an elasticity of the tissue, separating a first portion of the tissue from a second portion of the tissue, and severing the tissue from bone.

The method can vary in any number of ways. For example, the energy can be applied to at least one of a spinal disc, a ligament, and a facet joint. The spine can be surgically or non-surgically treated after the energy is applied. For example, performing the treatment can include non-invasively bracing the spine after the energy is applied to correct at least one of a curvature of the spine and a rotation of the spine. Performing the treatment can include non-invasively applying energy to the identified tissue to decrease a healing time of the identified tissue.

As another example, the modified tissue can include a spinal disc. Application of the focused energy can segment the spinal disc into a plurality of pieces. The treatment can include removing the pieces of the spinal disc from the disc space after the focused energy is non-invasively applied to the spinal disc.

In some embodiments, a method for treating a patient's spine includes imaging at least a portion of a patient's spine to identify scar tissue and/or an adhesion to be treated, the scar tissue and/or adhesion having been formed by a prior surgical procedure. The method can further include non-invasively applying energy to the identified scar tissue and/or adhesion from a location outside of the patient's body and performing a treatment on the patient's spine after the energy has been non-invasively applied.

Non-invasively applying the energy can be effective to separate the scar tissue and/or adhesion from at least one of a vessel, a nerve, and a dura of a patient. The identified scar tissue and/or adhesion can be formed in various areas of a patient, such as on an implant in the patient's spine. Performing the treatment can include performing a revision surgery. While various types of revision surgeries can be performed, in one embodiment the revision surgery includes removing the implant from the patient's spine.

In some embodiments, a method for correcting a spinal deformity in a patient includes imaging at least a portion of a patient's spine having a deformed region, non-invasively applying energy to tissue in proximity to the deformed region to modify the tissue and facilitate adjustment of vertebrae in the deformed region, and performing a treatment on the patient's spine after the energy has been non-invasively applied.

The modified tissue can include connective tissue of the spine and applying the energy severs or alters the elasticity of the modified tissue to facilitate adjustment of the vertebrae in the deformed region. Performing the treatment can include implanting one or more fixation devices in the patient to maintain the vertebrae in a corrected position. Performing the treatment can include non-invasively bracing the patient's spine.

BRIEF DESCRIPTION OF THE DRAWINGS

The present invention will be more fully understood from the following detailed description taken in conjunction with the accompanying drawings, in which.

DETAILED DESCRIPTION

Systems and methods for non-invasively modifying tissue to facilitate subsequent treatment are disclosed herein. Such systems and methods can generally include imaging a target region of a patient and non-invasively applying energy to the target region to modify tissue therein. The energy can be applied using various techniques, such as focused energy ablation, focused ultrasound, focused radiation, and RF electromagnetic energy delivery. The non-invasive energy delivery can serve as a pre-treatment for a subsequent procedure, which can be invasive or non-invasive. The methods disclosed herein can be used to define a surgical access path, dissect scar tissue in advance of a revision surgery, strip soft tissue from bone, segment a spinal disc or other anatomical structure to facilitate removal, perform soft tissue release in connection with deformity correction procedures, separate implants from body tissues prior to revision surgery, or to perform any of a variety of other tasks that facilitate treatment.

Figure 1:
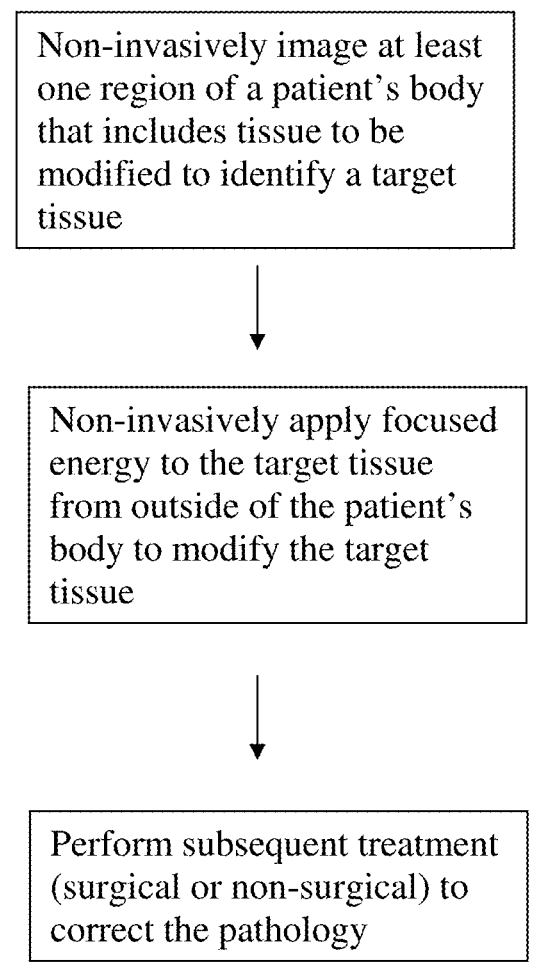
FIG. 1 is a flow chart of an exemplary method for correcting a pathology.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Methods disclosed herein can include the use of non-invasive imaging techniques in conjunction with one or more non-invasive techniques for modifying tissue, where "modifying tissue" includes, by way of non-limiting example, separating, ablating, obliterating, cutting, coagulating, cauterizing, segmenting, modulating the elasticity of, or otherwise altering one or more characteristics of the body tissue, including permanently modifying the tissue. Modifying the tissue can facilitate a subsequent non-invasive treatment of the body tissue. Modifying the tissue can also include "conditioning tissue," i.e., using one or more non-invasive energy application techniques to facilitate surgical treatment, such as to allow a surgeon to perform a surgery more efficiently and with reduced trauma and patient risk. As shown in FIG. 1, technology for non-invasively applying energy to tissue can be used in conjunction with imaging techniques to accomplish tissue dissection, separation of tissue, and/or modulation of mechanical properties of the tissue without requiring an incision in the patient. One exemplary type of ablation technology is focused ultrasound in which ultrasonic wave signals originating from different points outside of the body are focused to a common focal location within the body. As will be appreciated, the methods herein can be used as a stand-alone non-invasive treatment or can serve as a pre-treatment method that can facilitate performance of a subsequent surgical or non-surgical procedure on a patient's body, e.g., the spine. For example, the imaging and energy treatment of body tissue can be performed to facilitate navigating muscle and tissue to access a surgical site, prepare a surgical site for receiving an implant by stripping tissue from bone, and/or treating ligaments and tendons to facilitate surgical correction of bone. The modification of tissue in a non-invasive manner prior to performing a procedure can facilitate manipulation of tissue in and around the spine, improving clinical outcomes of a variety of spinal surgeries. Even when the non-invasive modification of tissue is not followed by a surgical procedure, the modification of tissue in this manner can increase the effectiveness of any subsequent non-surgical treatments.

Exemplary imaging techniques are described below, followed by non-invasive techniques for modifying tissue and specific examples of applying these non-invasive techniques to treat a patient.

Imaging Techniques

High-quality imaging of body structures can assist a surgeon with distinguishing between anatomical structures and determining specific areas of tissue to be modified via non-invasive methods. Exemplary body structures for imaging can include the spinal cord, dura, intervertebral disc (annulus and nucleus), vertebrae, spinal ligaments, adjacent blood vessels, nerves, scar tissue, and muscles. One or more imaging techniques can be selected based on the specific type of tissue to be modified and the surrounding anatomical structures.

Exemplary techniques for imaging a target site can include magnetic resonance (MR), X-ray, computed tomography (CT), and ultrasound based technologies. Each of these imaging techniques can provide different benefits and can be more suitable for particular applications. Magnetic resonance imaging (MRI), for example, can allow for high-quality imaging of many tissue structures and provides ways to distinguish between said structures. CT is an X-ray based technology that can be used when detailed features of bones and calcified tissues are required. Fluoroscopy is another X-ray based technology that can be useful for confirming relative spatial information of bony structures and instruments. Ultrasound imaging can be useful when high resolution is not required and when cost and convenience are important factors. In some embodiments, high-quality images can be obtained by combining images from different sources or using different settings (commonly referred to as image fusion).

MRI is generally performed by applying a strong magnetic field to a region of interest, transmitting a radiofrequency (RF) pulse to the region, and detecting the returning RF signals, which provide the signal intensity and spatial localization information needed to create an image. A three-dimensional map of the region of interest can be created by scanning multiple adjacent planes, or "slices" which can then be reconstructed on a computer. The signal intensity that appears on the image depends on characteristics such as proton density (PD), longitudinal relaxation time (T1), transverse relaxation time (T2), and flow. Variable image contrast can be achieved by adjusting angles between the applied magnetic field, RF pulse direction (flip angle), and RF pulse sequences (number, strength, and timing of the RF and gradient pulses). Commonly used RF pulse sequences include the PD-weighted, T1-weighted, and T2-weighted spin-echo sequences. The PD-weighted spin-echo sequence can use a long pulse repetition time (TR>2000 ms) and short length of time to echo (TE<30 ms). The T1-weighted spin-echo sequence can use a short pulse repetition time (TR<1000 ms) and short length of time to echo (TE<30 ms). The T2-weighted spin-echo sequence can use a long pulse repetition time (TR>2000 ms) and long length of time to echo (>80 ms). Examples of commercially-available MRI systems can include: Signa 1.5T/3.0T (GE Healthcare); Achieva 1.5T/3.0T and Integra 1.5T (Philips Medical Systems); and MAGNETOM Avanto, Espree, Symphony, Trio, and Verio (Siemens).

MRI techniques can be tailored to optimize visualization depending on the tissue site and the particular tissue at interest. For example, PD-weighted sequences can show contrast between scar tissue and herniated disc material. Also, cerebrospinal fluid surrounding the spinal cord and nerve roots and young intervertebral discs show high intensity on T2-weighted sequences due to their high water content. MRI contrast and quality, i.e., contrast-to-noise ratio, can be improved by utilizing contrast agents. For another example, one or more contrast agents can be administered to a patient intravenously or orally. Gadolinium chelates, such as gadolinium diethylenetriaminepentaacetic acid (Gd-DTPA), are the most common and when administered intravenously, can cause the resulting MRI imaging to have greater distinction between vascularized and non-vascularized tissue structures. T1-weighted sequences can be particularly useful when a gadolinium contrast agent is used, as this combination can enhance visualization of scar tissue and blood vessels.

MRI techniques can include the use of magnetic resonance (MR) thermometry. Various MR thermometry techniques may be used to determine relative or absolute temperature in the region of interest and are described in detail by Rieke, V. et al., MR Thermometry. 2008, J Magn Reson Imaging 27(2): 376-390, which is incorporated herein by reference in its entirety. MR thermometry can be used during performance of ablation or other non-invasive tissue modification in accordance with the teachings herein to monitor for and prevent excessive temperature increases to sensitive tissue structures, and can also be used to verify that the region of interest is being modified. Generally, temperature measurements are made based on proton density, T1 and T2 relaxation times, magnetization transfer, diffusion, proton resonance frequency, and/or thermosensitive contrast agents.

In certain instances, it can be desirable for a surgeon to obtain detailed features of the bony elements of the spine. Since MRI has limitations for imaging bone due to its low water content, it may be preferable to use CT. Examples of commercially available CT systems useful for this purpose include Brilliance CT 40 (Philips). Where it may be important to obtain high-quality images of bone and soft tissues, techniques such as "image fusion" may be used to merge the images obtained from MRI with those from CT, for example, as described by Karlo, C. A. et al., *J. MR/CT image fusion of the spine after spondylodesis: A feasibility study.* 2010, European Spine Journal 19 (10), pp. 1771-1775 which is incorporated herein by reference in its entirety.

Non-Invasive Techniques for Modifying Tissue

Invasive surgical procedures require a surgeon to cut tissue with one or more cutting tools and that tissue be moved in order for the surgeon to reach a location of interest, e.g., the spine. The techniques disclosed herein, which can include energy-based therapies such as radiation therapy and ultrasound therapy, can involve transmission of energy non-invasively through bodily tissues from a location outside of the patient's body. This can allow for a variety of physical effects to be generated at a point of interest without cutting into or moving the tissue surrounding the point of interest.

Focused ultrasound (FUS) is one energy-based treatment that can be utilized to ablate or otherwise modify tissue surrounding the spine. FUS utilizes one or more sound waves with a frequency greater than 20,000 Hz that propagate through body tissue. When the wave(s) comes into convergence at the focal point, thermal, mechanical, chemical, and optical reactions can occur in the tissue. Thermal and mechanical effects, such as acoustic cavitation, are particularly useful in the context of spinal surgery.

The extent of the effects of FUS on tissue can be varied by adjusting the focus, intensity, and time of exposure to the tissue. One method of focusing ultrasound waves that is simple and inexpensive involves using a spherically curved ultrasound transducer with a fixed beam focus. To compensate for its lack of versatility, a flat transducer with an interchangeable acoustic lens system can be used. The acoustic lens enables variation of focusing properties such as focal length and focal geometry. However, a potential drawback of the acoustic lens system is that ultrasound waves undergo sonic attenuation due to absorption by the lens. In another embodiment, a phased-array transducer can be used, as the waves in this system do not undergo sonic attenuation. A phased-array transducer can send temporally-different sets of electronic signals to each specific transducer component, thus enabling beam-steering and focusing, which can move a focal spot in virtually any direction within physically allowed ranges. Regardless of the particular type of transducer used, the focal length can be determined by the radius of curvature of the lens(es). In general, the focal length is preferably long enough to reach the targeted tissues, but short enough to prevent loss of intensity and/or loss of focus due to sonic attenuation. In one exemplary embodiment, the focal length can be in the range of about 5 cm to 20 cm, more preferably in the range of about 7 cm to 15 cm.

Sonic intensity is useful for characterizing FUS and is determined by the beam cross-sectional area, pulse repetition sequence and frequency, and hydrophone voltage. High-Intensity FUS (HIFUS) is said to have occurred when spatial-average temporal-average intensity ($I_{SATA}$) is higher than 5 W/cm$^2$, which may be required to cause coagulation necrosis of body tissues. Sonic pressure (squared) is proportional to sonic intensity and can be an alternative method to characterize the power and energy of the signal, such as explained in Kim et al., *High-Intensity Focused Ultrasound Therapy: an Overview for Radiologists.* Korean J Radiol 2008; 9:291-302 which is incorporated herein by reference in its entirety. Other intensity measures used for characterizing FUS can include pulse-average (IPA), temporal-average (ITA), spatial-peak pulse average (ISPPA), and spatial-peak temporal-average (ISPTA).

FUS and HIFUS can be used in various ways to ablate or otherwise modify tissue. In general, tissue ablation occurs as a function of both the temperature to which the tissue is heated and how long the tissue is exposed to this heat level, referred to as "thermal dose." By focusing ultrasound waves at more than one place or by scanning the area of interest, a volume of tissue can be thermally ablated. At high enough acoustic intensities, cavitation (i.e., microbubbles forming and interacting with the ultrasound field) can occur. These microbubbles can oscillate and grow and can eventually implode. For example, during inertial cavitation, very high temperatures inside the bubbles occur, and the collapse is associated with a shockwave and jets that can mechanically damage tissue (also known as histotripsy). Another exemplary technique involves injecting microbubbles into the region of interest, reducing time and energy requirements for creating microbubbles in the tissue. Vlaisavljevich, E. et al., *The effect of histotripsy on tissues with different mechanical properties.* 2011, IEEE International Ultrasonics Symposium, IUS, art. no. 6293435, pp. 1490-1493, incorporated herein by reference in its entirety, describes use of a commercially-available focused ultrasonic transducer operating at 1 MHz with an aperture of 100 mm and focal length of 90 mm to determine the sonic pressure threshold required to induce inertial cavitation in a variety of body tissues using pulse repetition frequencies of 100 or 1000 Hz. At these settings, cavitation was achieved in all tissue types except bone.

The sonication volume for a fixed point using a typical HIFU system operating at 1.5 MHz is cylindrical shaped and has a 1-2 mm diameter and 5-20 mm length. However, larger sonication volumes can be achieved using phased-array transducers focusing on multiple points. Alternatively, coated 6 mm diameter lenses with a carbon nanotube filled polymer composite and using laser-generated HIFU operating at >15 MHz, can achieve cylindrical shaped volumes as small as 75 µm in diameter and 400 µm in length.

As will be appreciated, other types of energy can be applied non-invasively to tissue, such as focused radiation and radiofrequency electromagnetic waves.

Non-Invasive Techniques for Modulating Tissue Elasticity

Certain energy-based devices can be used to modulate or alter the elasticity of tissues, which can be desirable depending on the particular treatment to be performed on a patient. For example, a significant, dose-dependent decrease in the tensile stiffness of ligaments and tendons was demonstrated by Yeh, C.-L. et al., *Imaging monitored loosening of dense fibrous tissues using high-intensity pulsed ultrasound.* 2013, Physics in Medicine and Biology 58 (19), pp. 6779-6796, incorporated herein by reference in its entirety. Yeh has used pulsed-HIFU with exposure time from 5 min to 30 min, pulse lengths of 91 µs with a repetition frequency of 500 Hz, and peak rarefactional pressure of 6.36 MPa, where the corresponding average intensities were kept around 1606 W/cm$^2$ for ISPPA and 72.3 W/cm$^2$ for ISPTA. Thus, while not suggested by this article, modulating of tissue elasticity in and around the spine can facilitate subsequent surgical or non-surgical treatment of the spine.

The degree of elasticity of tissue can be monitored by a surgeon, in real-time and in vivo, using various ultrasound elastography techniques. The term "elastography" describes an ultrasound-based imaging technique whereby local tissue displacements are estimated by applying a quasi-static tissue deformation (i.e., compression or palpation) and comparing pre- and post-deformation sets of ultrasound radio frequency data. Currently, there are a number of different elastography techniques, including strain imaging, sonoelastography, 1D and 2D transient elastography, acoustic radiation force impulse (ARFI) imaging, supersonic shear imaging (SSI), and vibro-acoustography. For example it has been shown that the elastic modulus of tendons can be evaluated in vivo by shear-wave imaging, such as in DeWall, R. et al., *Visualizing tendon elasticity in an ex vivo partial tear model.* 2014, Ultrasound in Med. & Biol. 40 (1), pp. 158-167, which is incorporated herein by reference in its entirety. Accordingly, these ultrasound techniques can be applied to monitor various types of tissue.

Energy-based devices can also be used to decrease healing time and encourage connective tissue and bone bonding. For example, Lovric V. et al., *The effects of Low-intensity Pulsed Ultrasound on tendon-bone healing in a transosseous-equivalent sheep rotator cuff model.* 2013, Knee Surg Sports Traumatol Arthrosc 21, pp. 466-475, incorporated herein by reference in its entirety, shows that low-intensity pulsed ultrasound significantly improved bone density at the tendon-bone interface in a sheep rotator cuff repair study. Such techniques can be used to heal tissues after the tissue has been treated with energy, such as focused ultrasound ablation, or to treat tissue that has been damaged during a prior surgical procedure.

Systems for Directing Energy to Particular Areas of Tissue

To facilitate modification of tissue using non-invasive energy, the focal region of the energy source can be directed to a predetermined location, for example based on the acquired image of the region of interest. In one embodiment, a controlled robotic system that is integral to or has been registered to the imaging equipment can be used to assist with focusing the energy source at a desired location. Beasley, R., *Medical Robots: Current Systems and Research Directions.* 2012, Journal of Robotics; Su, H. et al., *High-field MRI-Compatible Needle Placement Robots for Prostate Interventions: Pneumatic and Piezoelectric Approaches*, In Advances in Robotics and Virtual Reality; Gulrez, T and Hassanien, A. eds. Springer-Verlag, 2011, and Cleary, K. et al., *Interventional robotic systems: Applications and technology state-of-the-art.* 2006, Minimally Invasive Therapy and Allied Technologies 15 (2), pp. 101-113, which are incorporated herein by reference in their entirety, describe several medical robotic systems that can be used to focus an energy source at a target location, such as when modifying tissue using focused ultrasound technology. The energy delivery system can be compatible with the imaging equipment used so that ablation and/or modification of the tissue can be performed concurrently and in real-time with imaging and/or thermometry. One commercially-available system is the Innomotion (Steribal s.r.o.), which is compatible with MRI and CT scanners. Other commercially available systems include the ROBIO™ EX (Perfint Healthcare Pvt. Ltd, Florence, Oreg.) CT or PET-CT-guided robotic positioning system, AcuBot for active needle insertion under CT or fluoroscopy, the B-Rob systems for needle placement using CT or ultrasound, the MRBot for MRI guided prostate procedures and ExAblate MR guided Focused Ultrasound (Insightec).

Methods for Non-Invasively Modifying Tissue to Facilitate Treatment

The methods herein can utilize any of the above-described imaging techniques and energy application technology to modify tissue (e.g., to separate, ablate, obliterate, cut, cauterize, coagulate, segment, and/or modulate the elasticity of the tissue, or otherwise temporarily or permanently alter the tissue). By way of example, a surgeon can use ultrasound technology to form a pathway in tissue to access the spine, strip tissue away from other tissues (e.g. muscles and tendons from bone such as a vertebra), and/or to facilitate correction of complex spinal deformities. In each of these examples, the ultrasound device can be operated from a location outside of the patient's body and without requiring an incision to be formed in the patient. As will be appreciated, any number of the energy application and imaging techniques described herein can be used in combination to modify tissue in and around the spine or other regions of a patient or subject.

Referring back to FIG. 1, an exemplary method can generally include the steps of obtaining an image of at least one region of a patient's body, e.g., the spine, that includes tissue to be modified to identify a target tissue using one or more of the imaging methods herein, and non-invasively (e.g., non-surgically) applying focused energy to the target tissue from a location outside of the patient's body such that the target tissue is modified. The use of non-invasive methods for treating tissue, such as HIFU, can facilitate performing a subsequent surgical or non-surgical treatment and can improve outcomes of the same, as described in the examples below.

EXAMPLE 1

Defining a Surgical Access Path

Depending on the location of a particular target site in a patient's body for a surgical procedure, there can be multiple ways to access the site. Preferred pathways for accessing a surgical site generally avoid vital structures such as nerves, blood vessels, or tumors. A preferred pathway for accessing the site can also be selected to preserve musculature and/or to identify critical landmarks or anatomical borders. Conventional methods of forming an access path often involve extensive exploratory dissection, which can cause unnecessary trauma to surrounding tissue.

Figure 2:
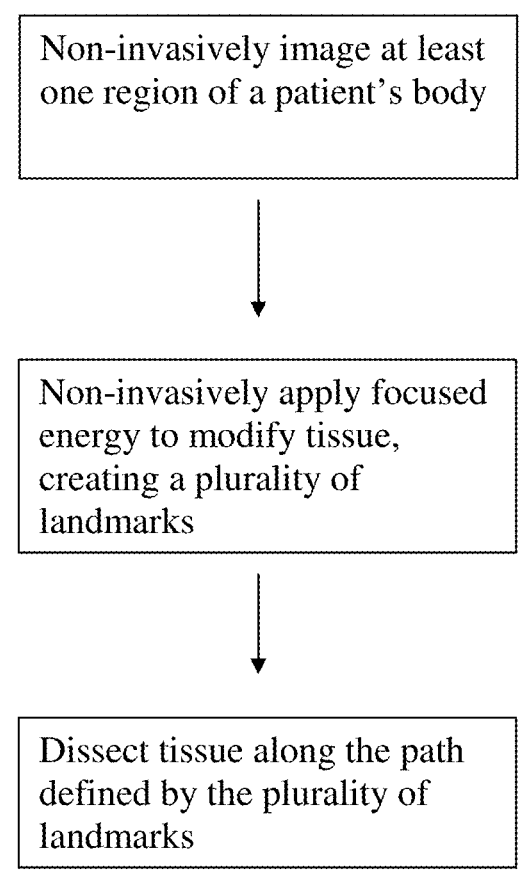
FIG. 2 is a flow chart of an exemplary method for forming a surgical access path.

The techniques described herein for non-invasively applying energy to tissue can be used prior to performing a surgical procedure on a patient to mark, chart, or otherwise define a pre-determined surgical access path. For example, as shown in FIG. 2, one or more images of a target site and an area proximate thereto in which a surgical access path is to be formed can be captured, e.g., using any of the imaging techniques described herein. The captured image(s) can then be analyzed to determine areas to be marked using non-invasive energy application to define a desired surgical access path. Focused energy can then be delivered to create a plurality of landmarks using any of the energy delivery techniques described herein, such as non-invasive tissue ablation that is performed using an ablation tool positioned outside of the patient's body. As previously mentioned, the energy can be applied without the need to form an incision in the patient. The type, mode, and duration of applying the energy can be selected based on the tissue and the type of markers that are to be created to define the desired surgical access path. Exemplary tissue which can be modified to define a landmark includes muscle, fat, tendons, ligaments, bone, etc. Application of energy to the tissue can cause physical changes to the tissue which can be observed by the surgeon as the surgical access path is created during a subsequent procedure. For example, the landmarks created by delivering energy to the tissue can have a visually-distinguishable color and/or texture from surrounding tissues.

Once the pathway has been charted by creating landmarks within the target area, the surgeon can form an incision in the patient and follow the landmarks to create the desired surgical access path. In other words, after the energy application is complete, a surgeon can simply follow the pathway defined by the modified tissue, with the modified tissue serving as a guide for the surgeon. A surgeon can dissect tissue and move toward the desired surgical site by following the modified tissues, eliminating the need for exploratory dissection. In addition, the use of non-invasive ablation treatment or other tissue modification can cause hemostasis in the ablated tissue, thereby decreasing bleeding during tissue dissection.

EXAMPLE 2

Revision Surgery

Following a surgical procedure, scar tissue and adhesions can form on vital structures such as blood vessels and nerves (e.g., dural or vascular adhesions). If revision surgery is needed, the scar tissue and adhesions make it very difficult and dangerous to access the target surgical site. In particular, it can be difficult for a surgeon to differentiate the scar from the vital structures and often, the scar tissue needs to be tediously dissected away. This can result in prolonged surgery time and other complications. By imaging the vital structures and performing non-invasive dissection of the scar tissue and adhesions prior to surgery, the surgical procedure can be made much safer and shorter.

Figure 3:
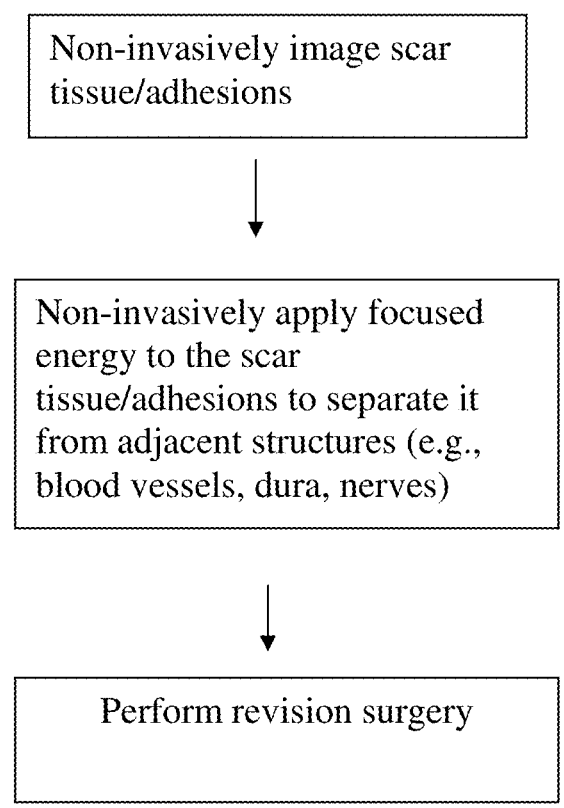
FIG. 3 is a flow chart of an exemplary method for modifying scar tissue and/or adhesions prior to a revision surgery.

As shown in FIG. 3, an exemplary method can include capturing one or more images of a target site at which a revision procedure is to be performed, e.g., using any of the imaging techniques described herein. The captured image(s) can then be analyzed to locate any scar tissue or adhesions that may exist at the target site. Focused energy can then be delivered to dissect the scar tissue or adhesions, thereby separating the scar tissue or adhesions from nearby structures such as vessels and nerves. When the surgeon later accesses the target site during the revision procedure, the need to delicately separate the scar tissue and adhesions can be obviated by the prior non-invasive dissection.

EXAMPLE 3

Stripping of Soft Tissue from Bone

In many different surgeries, muscle and tendons must be stripped off of the surface of bone. For example, in spinal procedures such as laminectomy or posterior scoliosis correction and fusion, muscle and tendons must be stripped from the lamina(e), the endplate(s), and/or other portions of the vertebra(e). This process can be very time consuming and can cause significant blood loss. Non-invasive stripping of muscle and tendons from the bony surfaces can be performed using any of the non-invasive energy application techniques described herein prior to performing the particular surgical treatment on the spine. High intensity focused ultrasound can be particularly useful for this application because it is effective at ablating muscle and tendon with minimal effects on surrounding bone.

Figure 4A:
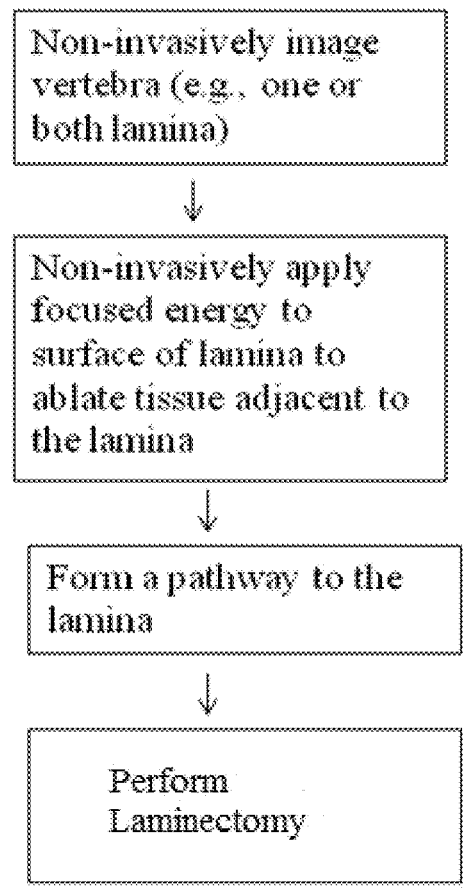
FIG. 4A is flow chart of an exemplary method for modifying tissue surrounding a lamina.
Figure 4B:
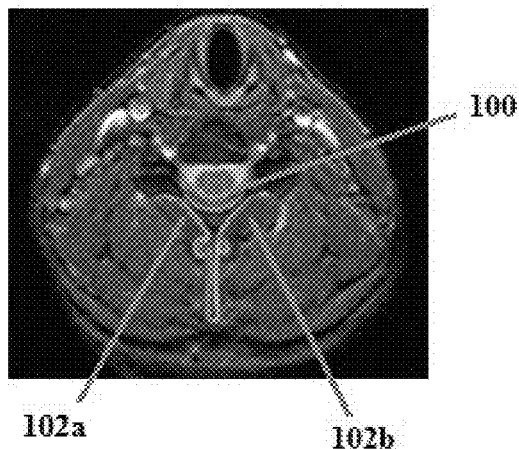
FIG. 4B is a cross-sectional view of a vertebra taken along an axis extending in a posterior-to-anterior direction in which energy has been delivered to laminae of the vertebra along an outer surface thereof to strip tissue from the vertebra.

An exemplary method for treating tissue surrounding a lamina in connection with a laminectomy procedure is shown in FIG. 4A. As shown, the target site (e.g., one or both laminae of a vertebra) can be imaged using any of the imaging techniques described above. The captured image can then be used to locate the laminar surfaces and to aim the energy delivery system. Energy can then be applied non-invasively to the surface of the lamina to separate or strip soft tissue attached thereto. Thereafter, a surgeon can form a pathway to the lamina and perform the laminectomy procedure using known techniques. FIG. 4B illustrates an exemplary vertebra 100, including first and second laminae 102$a$, 102$b$, having been modified using non-invasively applied energy to strip soft tissue therefrom.

EXAMPLE 4

Minimally Invasive Disc Removal

There are a number of procedures in which it can be necessary or desirable to remove some or all of an intervertebral disc. For example, during an interbody fusion procedure, the spinal disc can be removed from the intervertebral space and replaced with a spinal fusion cage or other implant delivered to the intervertebral space. The process of removing the spinal disc can be difficult and time consuming because the disc material needs to be stripped from the vertebral endplates and removed from the body to ensure that fusion occurs between the vertebrae. In addition, disc removal can be challenging in minimally-invasive procedures where visibility and access to the disc space are limited.

Figure 5A:
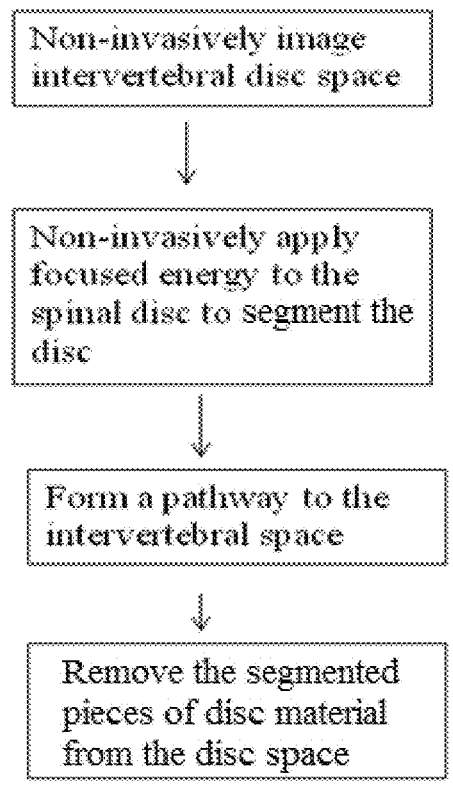
FIG. 5A is a flow chart of an exemplary method for non-invasively modifying a spinal disc to facilitate removal of the disc.

The energy application techniques herein (e.g., ablation) can be targeted at the spinal disc and can be used to segment the disc into multiple pieces that can easily be removed, such as using any one of a number of established minimally-invasive approaches through a cannula. An exemplary method for modifying tissue, e.g., a spinal disc, is shown in FIG. 5A. The method can include capturing an image of a disc space to locate a spinal disc or portion thereof that is to be removed. The method can also include using the captured image to aim an energy delivery device at the disc and to then deliver energy to the disc to segment the disc into plural pieces. The disc space can then be accessed surgically (e.g., via one or more cannulae or other minimally-invasive access portals) and the segmented pieces of the disc can be removed from the disc space.

Figure 5B:
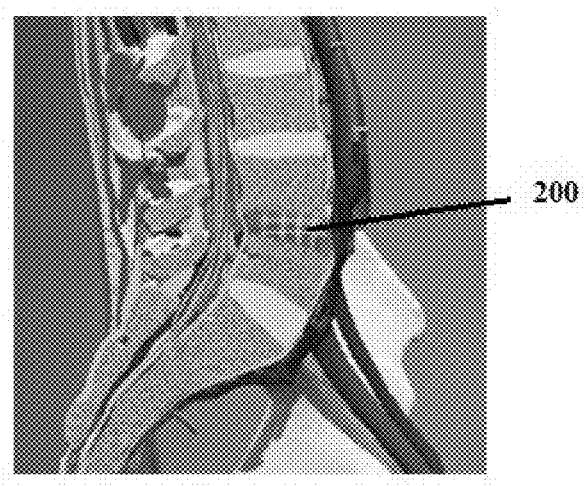
FIG. 5B is a lateral view of a spine, including a pattern of energy applied to an intervertebral disc space to segment the spinal disc disposed therein.

In some embodiments, energy can be delivered to a disc 200 in a grid pattern with cut or ablation lines that extend in a superior to inferior direction and in an anterior to posterior direction to segment the disc as shown in FIG. 5B. As will be appreciated, a surgeon can segment the disc into any number of pieces of various shapes and sizes or according to any of a number of patterns.

EXAMPLE 5

Non-Invasive Tissue Release

In some embodiments, energy can be applied non-invasively to modify tissue, e.g., release tissue to facilitate non-invasive deformity correction or condition tissue, e.g., release tissue to facilitate a subsequent surgical deformity correction. For example, energy can be applied to various types of tissue in the spine, such as the intervertebral disc, ligaments, and facet joints, in order to increase the flexibility of the spine prior to surgery or prior to non-surgical treatment such as bracing. This can be particularly useful in older patients with very stiff spines to enable better correction and global alignment and/or to prevent loosening of implants in softer bone (e.g., osteoporotic bone). This technique can also be useful in complex pediatric and adolescent scoliosis cases where there is severe curvature and/or rotation of the spine.

Figure 6:
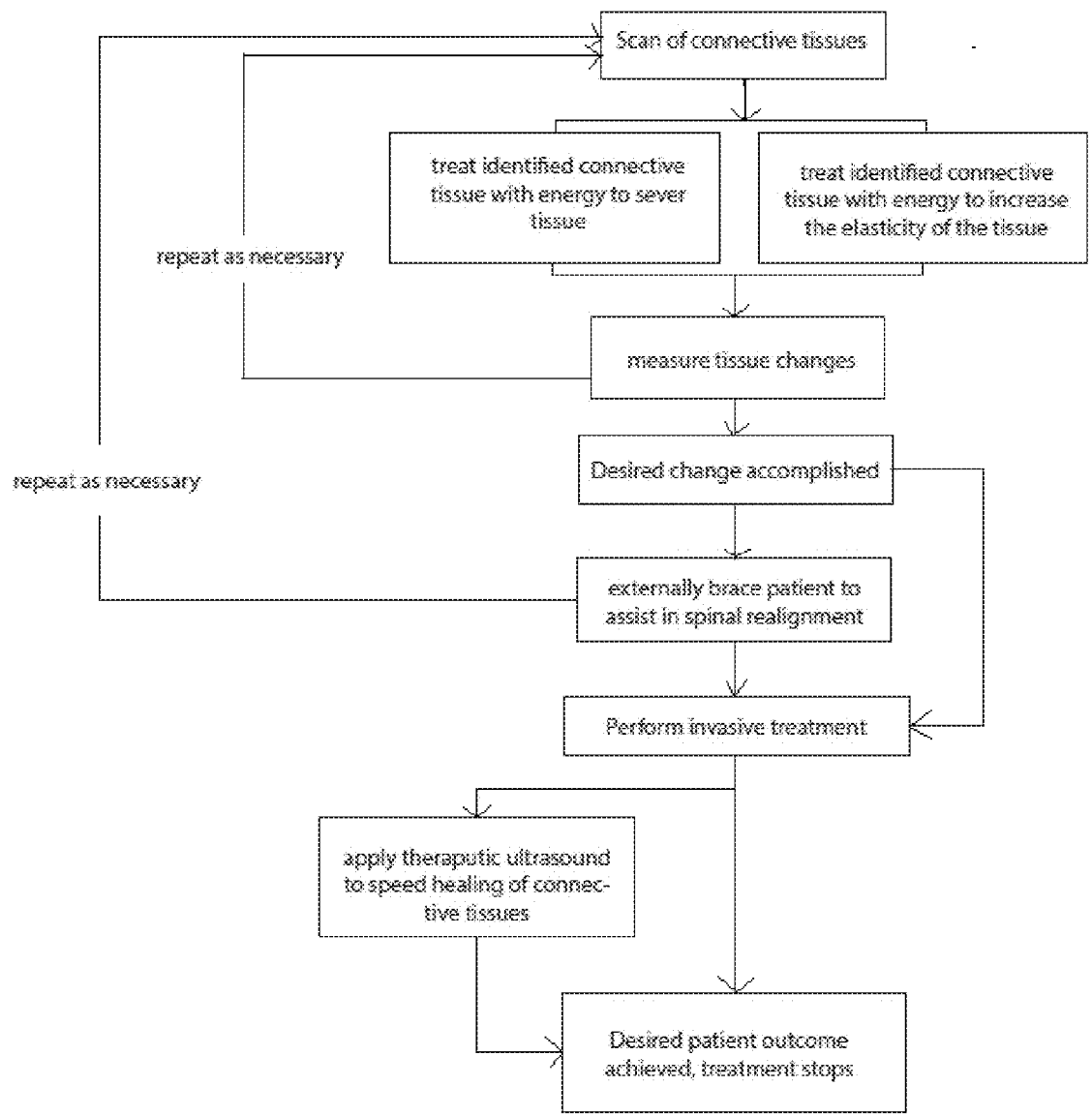
FIG. 6 is a flow chart of an exemplary method for non-invasively modifying tissue in the spine prior to performing an invasive surgical procedure.

In general, the non-invasive pretreatment of connective tissues before surgery can be targeted along curved areas of the spine to reduce the force necessary to manipulate the spine and to reduce the risk of nerve damage from overcorrection. With an image-guided energy based device such as MRI-guided pulsed HIFU, the elasticity of the connective tissues surrounding a scoliosis affected area of the spine can be non-invasively altered. FIG. 6 illustrates an exemplary method for modifying tissue that includes scanning connective tissue and applying energy to the tissue prior to performing a surgical procedure for treating a spinal deformity (e.g., scoliosis). As shown, the method can begin by imaging connective tissue in and around a curved region of a spine. The connective tissue can be non-invasively modified with any of the focused energy application techniques provided herein to facilitate subsequent correction of the spine. For example, focused energy can be applied to the connective tissue so that the tissue is severed or ablated. As another example, focused energy can be applied to the connective tissue to increase the elasticity of the tissue. During or after application of the focused energy, the change in the modified tissue can be approximated by the time and intensity of the treatment as described in *Imaging monitored loosening of dense fibrous tissues using high-intensity pulsed ultrasound* Chia-Lun Yehl, Pai-Chi Lil,Wen-Pin Shih, Pei-Shin Huang and Po-Ling Kuo, or measured directly using techniques like ultrasonic elastography as described in *Medical ultrasound: imaging of soft tissue strain and elasticity*, Peter N. T. Wells and Hai-Dong Liang. The imaging of the connective tissue and modification of the tissue with energy can be repeated as many times as is necessary until the desired change in the tissue is achieved.

Prior to performing a surgical treatment on the spine, the patient can optionally be fitted with an external brace to assist in spinal realignment. A single brace or a series of braces can be used to facilitate a gradual correction of the spine over a period of time, prior to performance of a surgical procedure. For example, serial casting is one alternative technique to standard bracing where a series of customized external braces are used to slowly correct a growing spine. This technique has been successful in treating patients under 20 months of age and with curves of less than 60 degrees. Once the spine begins to mature, existing casting and bracing techniques become less successful. The ability to manipulate a mature spine can increase the treatable age and degree of curvature that can be treated with casting and bracing treatments. With the use of an image guided energy based device like MRI guided pulsed-HIFU, the elasticity of the selected connective tissues in the spine can be manipulated or the tissue can be severed in a mature spine.

As shown in FIG. 6, the steps of imaging connective tissue, modifying the connective tissue with energy, and bracing the patient can also be repeated as many times as is necessary to obtain a desired degree of realignment in the spine. Alternatively, the patient need not be braced after the energy is applied and the non-invasive modification of the tissue with energy can still facilitate surgical correction of the spine. In either case, a surgical procedure can be performed on the spine to correct its curvature after the connective tissue has been non-invasively modified with energy. As will be appreciated, the procedure can be an open procedure or a minimally invasive procedure. The surgical procedure is optionally a robot-assisted procedure. While the surgical procedure can vary in any number of ways, the procedure can generally include forming one or more incisions in a patient, inserting one or more screws into one or more vertebrae, and attaching one or more fixation rods to the plurality of screws to internally brace the spine and remove the curved region. During or after the procedure is complete, ultrasound energy can be non-invasively applied to areas surrounding the implants to facilitate healing of the connective tissues. This can ensure that the connective tissue both heals around the implants and resists the natural tendency of the spine to return to its prior curved configuration.

Figure 7:
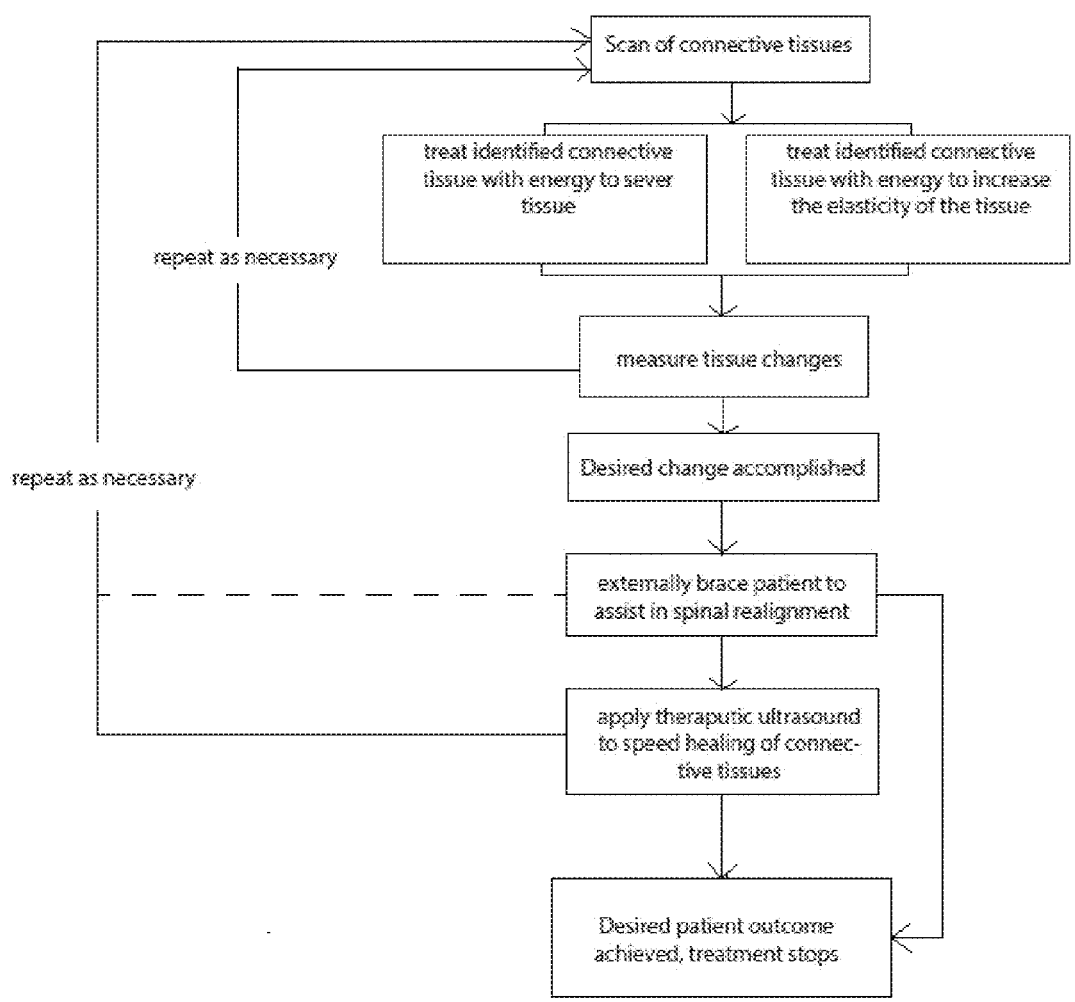
FIG. 7 is a flow chart of an exemplary method for non-invasively modifying tissue in the spine prior to performing a subsequent non-invasive treatment such as bracing.

Traditional non-invasive treatments of the spine can be augmented with non-invasive, energy-based modulation of the connective tissues in the spine. This energy-based treatment can include any of the non-invasive energy application techniques described herein and can be combined with bracing. The bracing can be performed a single time or can be repeated multiple times to allow for incremental adjustment, providing time for the body to adjust and reducing nerve stretch. For example, FIG. 7 illustrates a method that includes using both non-invasive energy application and non-invasive, external bracing to non-invasively treat a spinal deformity (e.g., scoliosis). As in the previous embodiment, the method can begin by imaging connective tissue in and around a curved region of a spine. The connective tissue can be non-invasively modified with any of the focused energy application techniques provided herein to modify the tissue and facilitate subsequent correction of the spine. For example, focused energy can be applied to the connective tissue so that the tissue is severed or ablated. As another example, focused energy can be non-invasively applied to the connective tissue to increase the elasticity of the tissue. During or after the focused energy is applied, the change in the treated tissue can be approximated by the time and intensity of the treatment as described in *Imaging monitored loosening of dense fibrous tissues using high-intensity pulsed ultrasound* Chia-Lun Yehl, Pai-Chi Lil,Wen-Pin Shih, Pei-Shin Huang and Po-Ling Kuo, or measured directly using techniques like ultrasonic elastography as described in *Medical ultrasound: imaging of soft tissue strain and elasticity*, Peter N. T. Wells and Hai-Dong Liang. The imaging of the connective tissue and modification of the tissue with energy can be repeated as many times as is necessary until the desired change in the tissue is achieved. As a first example, the non-invasive treatment of the patient can be complete after the desired change in the tissue is accomplished. Thus, in this example, the application of non-invasive energy can be used on its own to treat the curvature of the spine. As a second example, the application of non-invasive energy can be combined with other non-invasive techniques, such as the external bracing techniques previously mentioned. The use of non-invasive external bracing can be performed on the patient to further assist with realignment of the spine. During or after the application of the energy, or during or after the external bracing has been completed, optionally ultrasound energy can be non-invasively applied to areas surrounding the implants to facilitate healing of the connective tissues. This can ensure that the connective tissue both heals around the implants and resists the natural tendency of the spine to return to its prior curved configuration. When the spine has achieved a desired degree of realignment, the treatment is complete.

EXAMPLE 6

Separating Tissue from Implants

In some revision surgeries, it can be desirable to remove a device previously implanted in a patient, or to adjust or reposition a device previously implanted in the patient. There are a number of difficulties that can arise during such surgeries that can increase the length of the surgery and the associated risks. As an example, it can be difficult to remove screws implanted in a patient's vertebra in part due to growth of bone and tissue and/or the formation of scar tissue from the prior surgical procedure. In some embodiments, an implant (e.g., one or more tissue-facing surfaces of the implant) can be treated non-invasively using any of the energy application techniques herein prior to performing the revision surgery. Such treatment can be effective to separate the adjacent body tissues from the implant, thereby facilitating removal, repositioning, or adjustment of the implant. Exemplary implants to which energy can be applied include artificial discs, bone anchors, pedicle screws, bone plates, spinal fixation rods, and the like.

Figure 8:
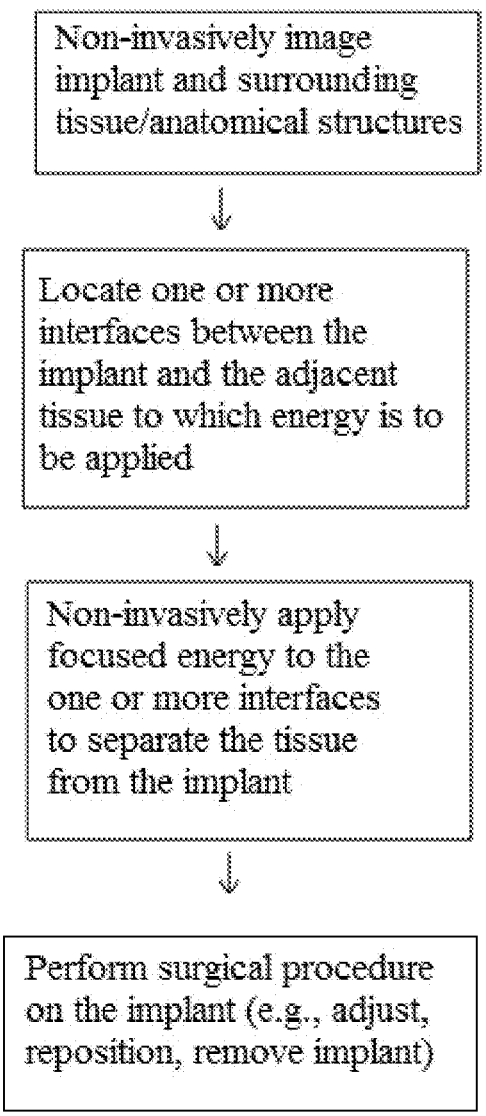
FIG. 8 is flow chart of an exemplary method for separating tissue from an implant.

An exemplary method for non-invasively separating tissue from an implant is shown in FIG. 8. As shown, the implant and the surrounding anatomy can be imaged using any of the imaging techniques described above. The captured image can then be used to locate one or more interfaces between the implant and the tissue to which energy is to be targeted, and to aim the energy delivery system. Energy can then be applied non-invasively to the implant and/or to the tissue to separate or strip the tissue away from the implant. Thereafter, a surgeon can form a pathway to the implant and remove, adjust, or reposition the implant, or perform any other manipulation of the implant that may be desired.

It should be noted that any ordering of method steps implied by the foregoing description or associated figures is not to be construed as limiting the method to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention. Furthermore, two or more of the method steps can be performed simultaneously.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for correcting a pathology, comprising:
imaging at least one region of a patient's body that includes tissue to be modified to identify a target tissue;
non-invasively applying focused energy to the target tissue from a location outside of the patient's body to modify the target tissue; and
after the target tissue has been modified, performing a treatment on the patient to correct the pathology;
wherein modifying the target tissue facilitates performing the treatment.

2. The method of claim 1, wherein application of the focused energy alters the elasticity of the tissue.

3. The method of claim 2, wherein application of the focused energy increases the elasticity of the tissue.

4. The method of claim 1, wherein application of the focused energy ablates the tissue.

5. The method of claim 1, wherein imaging the at least one region of the patient's spine is performed using at least one of MRI, CT, fluoroscopy, and ultrasound.

6. The method of claim 1, wherein the focused energy is applied using at least one of focused energy ablation, focused ultrasound, focused radiation, and RF electromagnetic energy delivery.

7. The method of claim 1, wherein application of the energy defines an access path.

8. The method of claim 7, wherein application of the energy causes the tissue along the access path to be visually distinguishable from surrounding tissue that has not been treated with focused energy.

9. The method of claim 7, wherein modifying the tissue comprises creating a plurality of landmarks to define the access path.

10. The method of claim 9, wherein the treatment comprises surgically dissecting the tissue along the path defined by the plurality of landmarks.

11. The method of claim 1, wherein applying the energy is effective to strip soft tissue off of a bone structure of the patient.

12. The method of claim 11, wherein the bone structure is a lamina of the patient and wherein the treatment comprises a laminectomy performed on the patient after the soft tissue is stripped from the lamina.

13. The method of claim 1, wherein the target tissue comprises tissue adjacent to a device implanted in the patient and wherein application of the focused energy separates the target tissue from the device.

14. The method of claim 1, wherein the target tissue comprises scar tissue and/or an adhesion and application of the focused energy separates the scar tissue and/or adhesion from at least one of a vessel, a nerve, and a dura of a patient.

15. A method for treating a patient's spine, comprising:
imaging at least a portion of a patient's spine to identify tissue to be treated;
non-invasively applying energy to the identified tissue from a location outside of the patient's body to modify the tissue; and
performing a treatment on the modified tissue after the energy has been non-invasively applied;
wherein the non-invasive application of energy facilitates the treatment.

16. The method of claim 15, wherein modifying the tissue comprises at least one of altering an elasticity of the tissue, separating a first portion of the tissue from a second portion of the tissue, and severing the tissue from bone.

17. The method of claim 15, wherein applying the energy comprises applying the energy to at least one of a spinal disc, a ligament, and a facet joint.

18. The method of claim 15, wherein performing the treatment comprises non-invasively bracing the spine after the energy is applied to correct at least one of a curvature of the spine and a rotation of the spine.

19. The method of claim 15, wherein performing the treatment comprises non-invasively applying energy to the identified tissue to decrease a healing time of the identified tissue.

20. The method of claim 15, wherein the modified tissue comprises a spinal disc.

21. The method of claim 20, wherein application of the focused energy segments the spinal disc into a plurality of pieces.

22. The method of claim 21, wherein the treatment comprises removing the pieces of the spinal disc from a disc space after the focused energy is non-invasively applied to the spinal disc.

23. A method for treating a patient's spine, comprising:
- imaging at least a portion of a patient's spine to identify scar tissue and/or an adhesion to be treated, the scar tissue and/or adhesion having been formed by a prior surgical procedure;
- non-invasively applying energy to the identified scar tissue and/or adhesion from a location outside of the patient's body; and
- performing a treatment on the patient's spine after the energy has been non-invasively applied.

24. The method of claim 23, wherein non-invasively applying the energy is effective to separate the scar tissue and/or adhesion from at least one of a vessel, a nerve, and a dura of a patient.

25. The method of claim 23, wherein the identified scar tissue and/or adhesion is formed on an implant in the patient's spine.

26. The method of claim 25, wherein performing the treatment comprises performing a revision surgery.

27. The method of claim 26, wherein the revision surgery includes removing the implant from the patient's spine.

28. A method for correcting a spinal deformity in a patient, comprising:
- imaging at least a portion of a patient's spine having a deformed region;
- non-invasively applying energy to tissue in proximity to the deformed region to modify the tissue and facilitate adjustment of vertebrae in the deformed region; and
- performing a treatment on the patient's spine after the energy has been non-invasively applied.

29. The method of claim 28, wherein the modified tissue comprises connective tissue of the spine and applying the energy severs or alters the elasticity of the modified tissue to facilitate adjustment of the vertebrae in the deformed region.

30. The method of claim 28, wherein performing the treatment comprises implanting one or more fixation devices in the patient to maintain the vertebrae in a corrected position.

31. The method of claim 28, wherein performing the treatment comprises non-invasively bracing the patient's spine.

\* \* \* \* \*